US012768840B2

(12) United States Patent
Penake et al.

(10) Patent No.: US 12,768,840 B2
(45) Date of Patent: Oct. 20, 2026

(54) METHOD FOR MONITORING AND PREVENTING CLINICALLY SIGNIFICANT KETONE LEVELS IN PATIENTS RECEIVING DICHLOROACETATE CO-ADMINISTERED WITH A CARBOHYDRATE RESTRICTED DIET

(71) Applicants: SAOL INTERNATIONAL DEVELOPMENT LTD., Hamilton (BM); University of Florida Research Foundation, Incorporated, Gainesville, FL (US)

(72) Inventors: David Penake, Atlanta, GA (US); Susan Clement, Zionsville, PA (US); John Devane, Dublin (IE); Sharon Hamm, Odessa, FL (US); Peter Stacpoole, Gainesville, FL (US); Richard Wagner, Bloomington, IN (US)

(73) Assignees: SAOL INTERNATIONAL DEVELOPMENT LTD., Hamilton (BM); UNIVERSITY OF FLORIDA RESEARCH FOUNDATION, INCORPORATED, FL (US)

( * ) Notice: Subject to any disclaimer, the term of this patent is extended or adjusted under 35 U.S.C. 154(b) by 0 days.

(21) Appl. No.: 19/217,991

(22) Filed: May 23, 2025

(65) Prior Publication Data

US 2025/0369974 A1 Dec. 4, 2025

Related U.S. Application Data

(60) Provisional application No. 63/659,494, filed on Jun. 13, 2024, provisional application No. 63/653,505, filed on May 30, 2024.

(51) Int. Cl.
*A61K 31/19* (2006.01)
*A61P 3/00* (2006.01)
*G01N 33/64* (2006.01)

(52) U.S. Cl.
CPC ............ *G01N 33/64* (2013.01); *A61K 31/19* (2013.01); *G01N 2800/52* (2013.01)

(58) Field of Classification Search
CPC ............ C07C 53/16; A61K 31/19; A61P 3/00
See application file for complete search history.

(56) References Cited

U.S. PATENT DOCUMENTS

| | | | |
|---|---|---|---|
| 9,765,393 | B2 | 9/2017 | Langaee et al. |
| 2013/0090382 | A1 | 4/2013 | Langaee et al. |
| 2021/0283072 | A1 | 9/2021 | Falk et al. |
| 2021/0322358 | A1 | 10/2021 | Tarnopolsky |
| 2025/0223628 | A1 | 7/2025 | Penake et al. |

OTHER PUBLICATIONS

NCT02616484 Trial of Dichloroacetate in Pyruvate Dehydrogenase Complex deficiency (DCA/PDCD), version of Sep. 12, 2022.*

Blackshear et al., "The Metabolic Effects of Sodium Dichloroacetate in the Starved Rat," *Biochem. J.*, 142, 1974, pp. 279-286.

Blackshear et al., "Metabolic Interactions of Dichloroacetate and Insulin in Experimental Diabetic Ketoacidosis: Studies on Whole Animals and After Functional Hepatectomy," *Biochem. J.*, 146, 1975, pp. 446-557.

Sofou et al., "Ketogenic diet in pyruvate dehydrogenase complex deficiency: short- and long-term outcomes," *J. Inherit Metab Dis*, 40, 2017, pp. 237-245.

Sheikh-Ali et al., "Can Serum β-Hydroxybutyrate Be Used to Diagnose Diabetic Ketoacidosis," *Diabetes Care*, 4, Apr. 2008, pp. 643-647.

Schwartz et al., "Treatment of glioma patients with ketogenic diets: report of two cases treated with an IRB-approved energy-restricted ketogenic diet protocol and review of the literature," *Cancer & Metabolism*, 3.3, 2015, pp. 1-10.

Woolf et al., "The Ketogenic diet for the treatment of malignant glioma," *Journal of Lipid Research*, vol. 56, 2015, pp. 5-10.

Zuccoli et al., "Metabolic management of glioblastoma multiforme using standard therapy together with a restricted ketogenic diet: Case Report," *Nutrition & Metabolism*, 7:33, 2010, pp. 2-7.

Langaee et al., "Personalized Dosing of Dichloroacetate Using GSTZ1 Clinical Genotyping Assay," *Genetic Testing and Molecular Biomarkers*, 22:4, 2018, pp. 266-269.

International Search Report and Written Opinion dated Jul. 28, 2025 issued in PCT/US2025/030848.

Gilbert et al., "The Ketogenic Diet: Seizure Control Correlates Better With Serum β-Hydroxybutyrate Than With Urine Ketones," *J Child Neurol.* Dec. 2000 Dec. 15(12 ):787-90. doi: 10.1177/088307380001501203. PMID: 11198492.

Lee et al., "Combined Treatment of Dichloroacetic Acid and Pyruvate Increased Neuronal Survival after Seizure," *Nutrients*, Nov. 13, 2022;14(22):4804. doi: 10.3390/nu14224804. PMID: 36432491: PMCID: PMC9698956.

Pan et al., "Human Brain β-Hydroxybutyrate and Lactate Increase in Fasting-Induced Ketosis," *J Cereb Blood Flow Metab.* Oct. 2000: 20(10):1502-7. doi: 10.1097/0000464 7-200010000-00012. PMID: 11043913.

International Search Report and Written Opinion dated Feb. 26, 2025, issued in PCT/US2025/010588.

Langaee et al., "The influence of human GSTZ1 gene haplotype variations on GSTZ1 expression," *Pharmacogenet Genomics*, May 2015, pp. 239-245.

Debrosse et al., Spectrum of neurological and survival outcomes in pyruvate dehydrogenase complex (PDC) deficiency: Lack of correlation with genotype, *Molecular Genetics and Metabolism*, 107, 2012, pp. 394-402.

(Continued)

*Primary Examiner* — Irina Neagu
(74) *Attorney, Agent, or Firm* — Greenblum & Bernstein, P.L.C.

(57) ABSTRACT

Methods of controlling unhealthy levels of beta-hydroxybutyrate during dichloroacetate administration by managing diet are disclosed.

1 Claim, 1 Drawing Sheet

(56) References Cited

OTHER PUBLICATIONS

Patel et al., "The spectrum of pyruvate dehydrogenase complex deficiency: Clinical, biochemical and genetic features in 371 patients," *Molecular Genetics and Metabolism*, 106, 2012, pp. 385-394.
Stacpoole et al., "Evaluation of Long-term Treatment of Children With Congenital Lactic Acidosis With Dichloroacetate," *Pediatrics*, vol. 121, No. 5, May 2008, e1223-e1228.
Dunbar et al., "Phase 1 trial of dichloroacetate (DCA) in adults with recurrent malignant brain tumors," *Invest New Drugs*, 32(3), Jun. 2014, pp. 452-464.
Michelakis et al., "Inhibition of pyruvate dehydrogenase kinase improves pulmonary arterial hypertension in genetically susceptible patients," *Sci. Transl. Med.*, 9; eaao4583, Oct. 25, 2017.
Abdelmalak et al., "Long-Term Safety of Dichloroacetate in Congenital Lactic Acidosis," *Molecular Genetics and Metabolism*, 109, 2013, pp. 139-143.
Berendzen (Mitochondrion 6 (2006) 126-135).
Stacpoole (Advanced Drug Delivery Reviews 60 (2008) 1478-1487).
Stacpoole (Mitochondrion 42 (2018) 59-63).
Ganetzky et al., "Primary Pyruvate Dehydrogenase Complex Deficiency Overview," Gene Reviews, Jun. 17, 2021, 18 pages.
PDCD FDA Listening Session, Sep. 8, 2023, 5 pages.
Stacpoole et al., "Controlled Clinical Trial of Dichloroacetate for Treatment of Congenital Lactic Acidosis in Children," Pediatrics, 117(5):1519-1531 (2006).
Wild et al., "Machine Learning Improves the Predictive Utility of Lactic Acid in Hospitalized Infants," medRxiv, pre-print publication, Apr. 3, 2025, https://doi.org/10.1101/2025.04.01.25321818, 20 pages.
Mongi Ayat, "Dichloroacetate is Promising for Treating Hematological Malignancy through Inhibiting Ketone Bodies Oxidation: towards Better Understanding of Its Anticancer Mechanisms", American Journal of Cancer Prevention, 2018, vol. 6, No. 1, pp. 5-8.
Jirair Bedoyan, "Pyruvate dehydrogenase complex deficiency", MediaLink Neurology, 2024.
P. Kaufmann et al., "Dichloroacetate causes toxic neuropathy in MELAS. A randomized, controlled clinical trial", Neurology, 2006, 66, pp. 324-330.
Rongrong Li et al., "Classic ketogenic diet-induced ketoacidosis in the treatment of pyruvate dehydrogenase deficiency: a case report and literature review", BMC Pediatrics, 2024, 24:603 (7 pages).

* cited by examiner

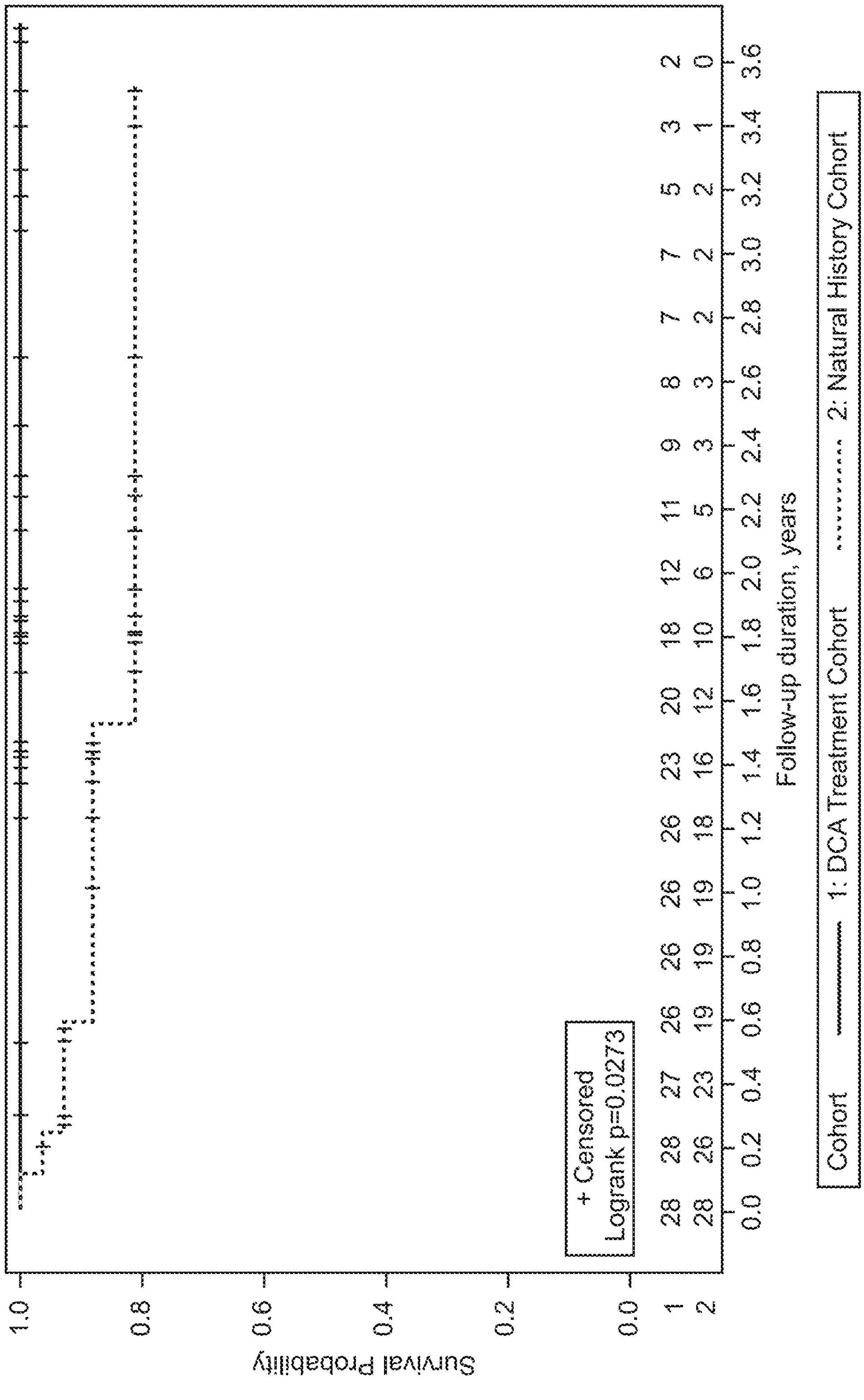
+ Censored
Logrank p=0.0273
Survival Probability
1.0
0.8
0.6
0.4
0.2
0.0
Follow-up duration, years
0.0 0.2 0.4 0.6 0.8 1.0 1.2 1.4 1.6 1.8 2.0 2.2 2.4 2.6 2.8 3.0 3.2 3.4 3.6
1 28 28 27 26 26 26 26 23 20 18 12 11 9 8 7 7 5 3 2
2 28 26 23 19 19 19 18 16 12 10 6 5 3 3 2 2 2 1 0
Cohort
1: DCA Treatment Cohort
2: Natural History Cohort

METHOD FOR MONITORING AND PREVENTING CLINICALLY SIGNIFICANT KETONE LEVELS IN PATIENTS RECEIVING DICHLOROACETATE CO-ADMINISTERED WITH A CARBOHYDRATE RESTRICTED DIET

CROSS REFERENCE TO RELATED APPLICATIONS

This application claims priority to the U.S. provisional application Nos. 63/653,505, filed May 30, 2024 and 63/659,494, filed Jun. 13, 2024, the entire contents of both of which are herein incorporated by reference.

STATEMENT OF GOVERNMENT SUPPORT

The invention was made with government support under grant numbers R01 HD087306 and R42 HD089804 awarded by the National Institutes of Health, and R01 FD007271 awarded by the United States Food and Drug Administration. The government has certain rights in the invention.

FIELD OF THE INVENTION

This invention relates to methods for controlling ketone levels in patients receiving dichloroacetate (DCA), and in some embodiments, when co-administered with a carbohydrate-restricted diet.

BACKGROUND OF THE INVENTION

Adverse effects from drug treatments are not uncommon. A first approach to minimizing adverse effects is to modify the dose of the drug, so that the adverse effects are lessened. However, in some instances, such dose-modification is unavailable. For instance, where the drug's dose is strictly limited by a patient's ability to metabolize the drug, or where the drug has a very narrow therapeutic window, other strategies should be considered.

SUMMARY OF THE INVENTION

The present invention provides methods for reducing the likelihood of clinically significant rises in ketone levels for patients being treated with DCA. In some embodiments, these patients are on or have the potential to be on a carbohydrate restricted diet.

In some embodiments, the patient has their Beta-hydroxybutyrate (BHB) level measured prior to initiation of DCA treatment.

In some embodiments, the patient has their BHB levels measured monthly for 3 months.

In some embodiments, the patient continues to have BHB levels measured if they reduce the number of carbohydrates in their diet or change their dose of DCA.

In some embodiments, the patient that has an increase in BHB levels is instructed to increase the portion of their calories that come from carbohydrates.

In some embodiments, the patients that do not experience an increase or reach clinically significant levels, monitoring is discontinued.

In some embodiments, the patients that are instructed to increase the amount of carbohydrates in their diet have BHB monitored until BHB stabilizes below about 3 mM.

Other features and advantages of the present invention will be set forth in the description of invention that follows, and will be apparent, in part, from the description or may be learned by practice of the invention. The invention will be realized and attained by the devices and methods particularly pointed out in the written description and claims hereof.

BRIEF DESCRIPTION OF THE DRAWINGS

FIG. 1 is a figure comparing the overall survival of the DCA-treated PDCD patients with untreated PDCD patients in a matched historical group.

DETAILED DESCRIPTION OF THE INVENTION

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

Ketogenic diets have shown therapeutic promise in multiple disease states including diabetes, oncology, epilepsy, and mitochondrial disorders. Ketogenic diets come in many forms, but the goal of the ketogenic diet is to increase the portion of calories ingested from sources of protein and fat while reducing the portion of calories ingested from sugar and carbohydrates. These diets are typically defined by at least half of total calories ingested coming from fats. These changes can alter energy metabolism in the body by making fatty acids the primary fuel for energy creation rather than sugars.

Sugars are converted to pyruvate and further converted to Acetyl-coenzyme-A (AcoA) by the pyruvate dehydrogenase complex (PDC). Once AcoA is formed into the mitochondria, it is catalyzed into energy using the citric acid cycle. In most organisms, the primary source of energy originates as carbohydrates. In people that have restricted carbohydrate diets, fatty acids are converted directly into AcoA as the primary source of metabolism for the body. This induces a preference for the breakdown of fat as the primary source of energy and therefore overall body metabolism. Clinically, this has been shown to be effective in disorders requiring glycemic control or disorders with increased precursors to mitochondrial respiration, in which the buildup of substrates may cause the body to create energy through the anaerobic glycolytic pathway, which can have harmful side effects, including lactic acidosis if over-utilized. Ketosis (utilization of fat rather than carbohydrate for energy) reduces the likelihood of this occurring because fatty acid conversion to AcoA bypasses most of the intermediate reactions where these problems take place and cannot be directly converted into a substrate for glycolysis.

Dichloroacetate (DCA) is a pyruvate dehydrogenase kinase (PDK) inhibitor that activates PDC and increases the conversion of pyruvate to AcoA. Clinically, this has been shown to reduce anaerobic glycolytic energy creation in multiple disease states and is being tested to see if it can help to mitigate some of the same challenges for which the ketogenic diet may provide benefit.

Beta-hydroxybutyrate (BHB) is a fatty acid that usually exists at low levels in the body. In patients that are on the ketogenic diet, these levels have a dose-dependent increase, meaning that the higher ratio of fat and protein calorie source to carbohydrate calorie source typically leads to higher the levels of BHB. BHB is one of the notable ketones, and in certain embodiments is used to monitor ketone levels generally.

Given the mechanism of action of DCA, it is believed that patients that ingest low levels of sugar should have modest metabolic alterations. In theory, if the body ingests a limited amount of sugar, the precursors of pyruvate should be minimal and likely only those created by gluconeogenesis to support energy needs in cells that do not have mitochondria (e.g., red blood cells). This suggests that despite the addition of DCA, which may increase the conversion of pyruvate to AcoA, if the substrate of pyruvate is minimal, there should be minimal benefit of DCA and energy metabolism should remain in homeostasis.

Blackshear et al. showed rises in ketone levels following administration of DCA in vivo, as DCA can reduce the rate of uptake of fatty acids into muscle in rats. The rises in ketone levels occur and are transiently reduced. BHB appears to rise more than acetoacetate and falls off more slowly, suggesting a reduction in lipolysis. In rats experiencing ketoacidosis, BHB rates appear to rise modestly and fell swiftly, while rats that had high levels of ketones but were not in acidosis appear to experience a longer duration rise in BHB. [Blackshear et al., *Biochem. J.* (1974) 142: 279-286; Blackshear et al., *Biochem. J.* (1975) 146:446-557]. In the human study of PDCD patients (NCT02616484), unlike the descriptions published by Blackshear, some patients experienced a rise in BHB levels while some did not. Those that experienced a rise in BHB levels, many experienced chronically elevated BHB levels, again, unlike what was published by Blackshear. Finally, there was no obvious way to predict which patients would experience elevated BHB levels and the increase in levels was not associated with baseline blood ketones. This relationship is described below:

Sofou [Sofou et al., *J. Inherit Metab Dis* (2017) 40:237-245], conducted an open label study on PDCD patients that followed each patient's progression of disease and development while tracking lactate levels and the degree of the ketogenic diet. The study stated: "Parents of eight patients replied, considering optimal plasma ketone levels as being >2 mmol/l, with a median of 3.3 (2.1-4.5) mmol/l. Almost all patients who were considered by investigators as being at least much improved had ketone levels of ~3-3.5 mmol/l, as opposed to the remaining patients, with ketone levels <3 or >4 mmol/l."

Once administered DCA, optimization of ketone levels is less important due to the increase flux of converting glucose into pyruvate and then AcoA. In the absence of flux, increases in sugars often lead to increases in lactate. As was described by Sofou, an optimized ketogenic diet manages lactate levels without creating acidic levels of ketones. This was described to lead to clinically important improvements. Following administration of DCA, a reduction in BHB levels does not reflect an increase in the glycolytic pathway and may not increase lactate levels. Keeping ketone levels below a clinically significant level and maintaining normal levels of lactate (below 2.0 mM) is desirable.

Sheikh-Ali et al [Sheikh-Ali et al. *Diabetes Care* 2008 Apr; 31(4):643-7] identified that in children with diabetes, BHB levels that exceeded 3.0 mM can be used to diagnose diabetic ketoacidosis and may be superior to other measures, such as serum $HCO_3$.

Ketogenic diets can be used in the treatment of many diseases. Due to the centrally acting mechanism of action of DCA, all potential indications in which increased metabolic efficiency could lead to a clinical improvement may be subject to a combination of a ketogenic diet and DCA. For example, articles by Schwartz, Zuccoli and Woolf [Schwartz et al. *Cancer & Metabolism* (2015) 3:3; Woolf and Scheck *Journal of Lipid Research* Volume 56, 2015, 5-10; Zuccoli et al. *Nutrition & Metabolism* 2010 7:33] describe the potential utility of a ketogenic diet in the treatment of glioblastoma multiforme and gliomas.

For patients that ingest high levels of carbohydrates, one would expect the energy balance following administration of DCA to favor mitochondrial oxidative phosphorylation versus glycolysis.

Therefore, regardless of the dietary regimen, it would be expected that long-term administration of DCA would maintain or decrease the long-term levels of free-fatty acids and ketones in the body.

DCA was studied in a Phase II clinical trial in patients with recurrent glioblastoma (NCT05120284). It is conceivable that many of these patients would be considered candidates for both treatments and therefore should be monitored for clinically significant ketone elevations due to the combined treatment.

A total of 30 (of the 34) patients in the Phase III study in PDCD patients had lab values that could be evaluated throughout the study. Of these 30, 24 were defined to be adherent to a ketogenic diet based on their BHB level at baseline to be >0.3 mM. These 24 patients had an average BHB of 2.68 mM and average lactate of 2.26 mM at baseline, prior to DCA or placebo intervention.

Following administration, 15 of the 24 patients adherent to the ketogenic diet had a rise in ketone levels after administration of DCA. Nine patients did not experience a rise in these levels after administration of DCA.

The 15 patients that experienced an increase while on DCA experienced an average rise in BHB levels from 2.19 mM (not on DCA) to 3.27 mM while on DCA. This is a 49% increase. The same group of patients had a rise in clinically significant levels of BHB (>3.0 mM) from 13% of the measurements (not on DCA) to 62% of the measures while on DCA. Overall, these patients experienced a drop in lactate levels of 20% while on DCA, consistent with a biochemical response to treatment. The percentage of patients with normal lactate levels (2.0 mM or less) increased from 33% (not on DCA) to 73% while on DCA.

The 9 patients that did not experience an increase in BHB levels while on DCA experienced a slight reduction. Their average levels dropped from 2.04 mM (not on DCA) to 1.8 mM while on DCA. The number of measures that exceeded 3.0 mM also dropped from 38% (not on DCA) to 24% while on DCA. Lactate also dropped in this population by 11%, suggesting a biochemical response. The percentage of patients with normal lactate levels (2.0 mM or less) increased from 51% (not on DCA) to 71% while on DCA.

Both groups of patients experienced an improvement in lactate levels with >70% in both groups achieving lactate normalization while on DCA therapy. In contrast, the group experiencing increases in BHB had nearly a 5-fold increase in the number of patients with levels of 3.0 mM or higher. Of these patients, 28% had BHB levels greater than 4.0 while on DCA versus only 3% while not on DCA. These increases are unexpected, chronic unless an intervention is taken, and noted by experts in the field to be detrimental to clinical outcomes.

The present inventors surprisingly discovered that administration of DCA, in some patients that had reported ketogenic diets ranging from 2:1 to 4.4:1, ratios of grams from fat to carbohydrates and protein resulted in significant and extended increases in the levels of BHB. In some cases, these levels exceeded levels commonly used to diagnose ketoacidosis, a serious clinical syndrome. It was also surprising that some patients had increases in the levels of BHB and others did not. These levels also do not appear to be dose- or exposure-dependent, and patients that experienced these increases could not be prospectively identified to reduce risk exposure.

In the study supporting this invention, DCA was used to treat PDC deficiency (PDCD). This is notable because the constellation of symptoms (lack of muscle tone, lethargy, high blood/plasma acidity) are common with ketoacidosis. These symptoms are also seen in a number of diseases of metabolism. This becomes particularly concerning as patients that are treated with DCA and have a carbohydrate-restricted diet may have consequences from ketoacidosis that are perceived to be the natural course of the disease of metabolism. In some of these cases, a slight alteration in diet could unmask significant clinical benefit.

Experiments by Blackshear presented earlier appear to show that DCA can raise levels of ketones in the body following administration for a short period of time and then quickly recovers. It is hypothesized that this is caused by two mechanisms. First, for fatty acids that have been mobilized to produce energy, there is a shift in energy production that reduces the use of ketones and therefore provides a temporary increase in free fatty acids. Secondarily, DCA can slow the oxidation and uptake of ketones for conversion to adipose tissue.

It is additionally important to note that DCA has a narrow therapeutic index and has been associated with a causal relationship with therapy limiting peripheral neuropathy adverse events. Langaee et al. [Langaee et al. *Genetic Testing and Molecular Biomarkers* 2018 22:4, 266-269] identified that the metabolism of DCA is primarily completed in the liver with the GSTZ1 enzyme. This enzyme has multiple haplotypes and several haplotypes slow the rate of metabolism of DCA, leading to a higher risk of adverse effects. In particular, five frequent GSTZ1 haplotypes are known: EGT (~50% of the population), KGT (~30% of the population), EGM (~15% of the population), KRT (~5% of the population), and KGM (~0.4% of the population). EGT is considered a fast metabolizer of DCA, while KGT, EGM, KRT, and KGM are considered slow metabolizers of DCA. EGT carriers (fast metabolizers) have been shown to have a low risk of peripheral neuropathy adverse events at dosages of 25 mg/kg/day and EGT non-carriers (slow metabolizers) experience the same at 12.5 mg/kg/day. Alternatively, dosages for fast metabolizers may be 20 mg/kg/day, 30 mg/kg/day, or 35 mg/kg/day, or any dosage therebetween, and dosages for slow metabolizers may be 5 mg/kg/day, 10 mg/kg/day, or 15 mg/kg/day, or any dosage therebetween. The dosage may be divided during the course of a day, for example, for a fast metabolizer, 12.5 mg/kg every 12 hours and for a slow metabolizer, 6.25 mg/kg every 12 hours. In rare cases, a 4th allele mutation may cause a substantial reduction in the metabolism of DCA that may require personalized dosing adjustments.

For fast metabolizers, the dose may be calculated by multiplying the patient's kilogram weight by the 12.5 mg/kg per 12 hours dose level and dividing by the concentration of the solutions (50 g/mL). The result is the dose in mL for administration using a medication administration device.

$$[\text{Body Weight (kg)} \times 12.5\ (\text{mg/kg dose level})]/50\ (\text{mg/mL}) = \text{Dose in mL}$$

For slow metabolizers, the dose may be calculated by multiplying the patient's kilogram weight by the 6.25 mg/kg per 12 hours dose level and dividing by the concentration of the solution (50 mg/mL). The result is the dose in mL for administration using a medication administration device.

$$[\text{Body Weight (kg)} \times 6.25\ (\text{mg/kg dose level})]/50\ (\text{mg/mL}) = \text{Dose in mL}$$

The DCA may be administered orally, such as by an oral route, a nasogastric tube route, or a gastric tube route, in the morning and evening. The DCA may be taken with or without food.

It should be noted that patients with the KGM haplotype, which results in an even slower metabolism than the other slow metabolizing haplotypes, should have regular monitoring for an increased risk of peripheral neuropathy.

Due to the differential metabolism of different haplotypes, DCA must be dosed using an individualized, genetic reading to maximize the risk/benefit ratio. Typically, lower doses are provided in the case of slow metabolizers of DCA, to reduce the likelihood of treatment-limiting toxicities. Because the dosing of DCA is made on an individualized patient basis, it is both impractical and potentially unsafe to alter dose of DCA simply to optimize ketones or BHB.

However, it is important to control the levels of ketones and BHB in such patients. In this regard, in the clinical study of DCA in PDCD patients supporting this invention, the rise in BHB became biochemically notable in a number of patients, particularly given that the increased rates of ketones and potential exposure to long-term ketoacidosis could occur. It is therefore important that the concurrent treatment of a ketogenic diet and dichloroacetate be monitored such that the diet, rather than the DCA dose, can be adjusted to prevent potential clinical consequences associated high and chronic levels of ketones.

In the Phase III clinical trial discussed below, some patients treated with DCA that also adhered to a ketogenic diet experienced significant rises in plasma BHB levels without experiencing acidosis. Therefore, plasma BHB levels should be monitored prior to initiation and during treatment. If an increase in BHB levels occurs, consideration should be given to increasing dietary carbohydrate levels to achieve the desired BHB maintenance level. Dosing of DCA, however, should not be empirically adjusted. Additional monitoring for ketoacidosis is also recommended, in line with routine ketogenic diet management.

The ability to manage a ketogenic diet has improved greatly with the addition of medical foods and prepackaged keto-friendly food options. In the past, patients using a strict diet needed to measure the majority of their food so as to maintain and calculate their dietary ratios. Now, companies offer product lines that support the ability to maintain a ketogenic diet with a reasonable degree of food variety. Additionally, many of the products have the same taste profile but are specially formulated for different ketogenic diet ratios. For example, a patient could choose to manage their diet using products made by the brand KETOCAL® (www.shop.myketocal.com). Their products are formulated to incorporate diets ranging from 2.5:1 to 4:1 (as of this filing). A competing brand, KETOVIE®, offers similar products including shakes and mixes but also incorporates keto friendly sweets, cereals and pizzas, each with a specific targeted ketogenic ratio. The product line for KETOVIE® can be found on their website (www.ketovie.com/products). There are multiple other resources for ketonic diet friendly products. Therefore, if a patient were to have clinically significant measures of ketone levels, the ketogenic diet can be reduced easily, in many cases through a like-for-like product substitution for the same product with a higher carbohydrate or protein content.

To reduce the invention to practice, the following is recommended. If a patient is identified as a candidate for DCA therapy, the prescribing physician or an expert should interview the patient or caregiver to understand what the patient's diet consists of and if the diet is one that would lead to higher (>0.3 mM) levels of ketones. Each of these patients should also receive a genetic haplotype test to identify the proper dose of DCA and have baseline levels of lactate and BHB taken prior to the initiation of therapy. Alternatively, the prescribing physician or an expert may interview the patient or caregiver to understand what the patient's diet consists of and if the diet is one that would lead to a ketone level of >0.1 mM, >0.2 mM, >0.4 mM, or >0.5 mM, or any level therebetween. Once the results are back, the physician or expert should consult the patient about 1) DCA therapy and how that may alter the fuels used by the body to support metabolism, 2) that DCA has been shown to cause substantial increases in chronic ketone levels in some patients following administration of DCA, 3) describe what some of the symptoms are for high levels of ketones or ketoacidosis and how depending on the condition, it may be similar to what the patient experienced from the disease, and 4) that monitoring should be done regularly to change the dietary regimen if ketone levels exceed 3.0 mM when lactate is below 2.0 mM. If lactate remains above 2.0 mM following DCA administration, the diet should be adjusted to have the best balance of outcomes—likely a BHB of 3.5 mM or less. Alternatively, the diet can be adjusted to have a BHB level of 2.9 mM or less, 2.8 mM or less, 2.7 mM or less, 2.6 mM or less, 2.5 mM or less, or 3.5 or more, such as 3.6 mM, 3.7 mM, 3.8, 3.9 mM, or 4.0 mM, or higher if needed. For patients with severe metabolic deficits, these optimized levels may not be able to be reached and the best clinical judgement should be used.

It should be noted that BHB may be monitored on a regular "check-in" basis. For example, such monitoring of BHB may conducted on a weekly basis, a biweekly basis, a monthly basis, a bimonthly basis, quarterly, etc. When monitoring BHB, attention should be paid to whether a significant change in BHB levels has been observed. A "significant change" can be an increase or decrease of, for example, 10%, 20%, 30%, 40%, 50%, or greater than 50% relative to a prior measurement.

Following this consult, dosing of DCA should be initiated at the dosage identified based on the genetic haplotype testing. The patient should be scheduled for regular lab visits and the patient should be instructed to maintain a steady diet during this period. DCA has been shown to increase ketone levels quickly based on literature and chronically based on results of the Phase III study. Therefore, it is plausible to take lactate and BHB levels after 2 weeks, 4 weeks and monthly thereafter until the best clinical results of lactate and BHB has been identified. If after two measurements, the patient has not had a spike in their BHB levels, additional monitoring beyond regularly scheduled physician visits will not be required unless the patient initiates a carbohydrate restricted diet or begins taking a more restrictive diet. If an increase in BHB is identified, physicians should work with the patient to add carbohydrates as a percentage of the diet and take another test in 2 weeks. It is recommended that patients alter their diet in a stepwise fashion. If a patient has a diet that exceeds 4:1, it is recommended that carbohydrates be increased to bring the patient to a 4:1 ratio. If they are between 3:1 and 4:1, they are recommended to adhere to a 3:1 ratio. If between 2.5:1 and 3:1, it is recommended that they adhere to a 2.5:1 ratio. If the patient is at or below a 2.5:1 ratio, has controlled lactate (below 2.0 mM) and high levels of BHB (>3.0 mM), it is recommended that the physician and patient seek to use further discretion at ratios less than 2.5:1, so as to maintain lactate at 2.0 mM or less at the lowest possible BHB level, even if it exceeds 3.0 mM.

Regular monitoring, for instance at each scheduled doctor visit, is encouraged to maintain lactate and BHB levels and confirm the correct course of action. As noted in the specific patient examples provided, lactate and BHB can be variable even with a consistent diet due to a variety of factors. The biochemical measurements should be used as a guide to support improved clinical decisions.

Although this will be commonly used in mitochondrial conditions where patients typically have increased systemic levels of lactate, in other conditions, such as certain forms of cancer, may only have increases in lactate that are local to the tumor and do not create systemically elevated levels. In these circumstances where a patient adheres to or initiates a ketogenic diet, the process may be the same to find the optimal dose. It is just that in most of those circumstances, the lactate level typically remain below 2.0 mM and the goal may be to identify the correct diet to support safe levels of circulating ketones as the primary target since lactate will likely remain within normal ranges. The process previously described for biochemical monitoring and dietary adjustment can be used and similar monitoring should be conducted.

The following examples are illustrative of the present invention, and are not to be construed as limiting the scope of the invention. Variations and equivalents of this example will be apparent to those of skill in the art in light of the present disclosure, the drawings, and the claims herein. Unless otherwise stated, all percentages are by weight of the total composition.

EXAMPLES

Example 1: Patient 03-001

This patient entered the study with a restrictive ketogenic diet. When the patient began taking DCA, their BHB rose dramatically and fell back below 3.0 again when the patient began taking placebo. After the study was completed, the patient reduced their ketogenic ratio to near 3:1 and was able to maintain stable lactate levels at BHB levels below 3.0. The patient remained on DCA therapy for over 900 days.

TABLE 1

| | Lactate (mM) | BHB (mM) | Keto Ratio (Calories from Fat: Carb + Protein) |
|---|---|---|---|
| Baseline | 1.59 | 2.71 | 3.4:1 |
| DCA | 1.25 | 4.21 | 4.0:1 |
| Placebo | 1.28 | 2.18 | 4.1:1 |
| DCA Open Label 1 | 1.36 | 4.41 | Not Recorded |
| DCA Open Label 2 | 1.16 | 2.76 | 3.2:1 |
| DCA Open Label 3 | 1.41 | 2.06 | 3.1:1 |

Example 2: Patient 01-001

This patient entered the study with elevated lactate and BHB while observing a strict ketogenic diet (3.5:1 ratio). When placed on DCA, despite a modest reduction in the ratio of calories from fat (3.1:1), their BHB rose dramatically to 6.36, a potentially clinically significant value. Despite this, their lactate fell to within the normal range. When the patient returned to placebo, the BHB was reduced and the lactate again returned to an elevated value. Their diet was not recorded prior to this measurement. In the open label portion of the study, the patient maintained a strict diet (4.0:1) with reasonably well controlled lactate and poorly controlled BHB. This patient may benefit from a less strict diet. This patient has been on therapy for more than 850 days.

TABLE 2

| | Lactate (mM) | BHB (mM) | Keto Ratio (Calories from Fat: Carb + Protein) |
|---|---|---|---|
| Baseline | 2.66 | 3.3 | 3.5:1 |
| DCA | 1.4 | 6.36 | 3.1:1 |
| Placebo | 2.12 | 3.58 | Not Recorded |
| DCA Open Label 1 | 1.58 | 3.19 | 4.0:1 |
| DCA Open Label 2 | 2.13 | 2.74 | 4.0:1 |
| DCA Open Label 3 | 1.33 | 4.08 | 4.0:1 |

Example 3: Patient 07-003-S

This patient entered the study with both BHB and lactate within normal ranges (0.69 and 1.65 respectively). This patient was able to maintain this through a 3:1 ratio ketogenic diet. During the study, the patient was first randomized to placebo and later received DCA. While on placebo, the lab values for the patient were similar. Once put on DCA, the lactate level was maintained near the upper limit of normal but the BHB level increased dramatically. The patient remained on a 3:1 ketogenic diet throughout the study but later reduced their diet to a normal Western diet (0.7:1) and has benefitted from this.

TABLE 3

| | Lactate (mM) | BHB (mM) | Keto Ratio (Calories from Fat: Carb + Protein) |
|---|---|---|---|
| Baseline | 1.65 | 0.69 | 3.0:1 |
| Placebo | 2.35 | 0.48 | 3.0:1 |
| DCA | 1.99 | 4.02 | 3.0:1 |
| DCA Open Label 1 | 0.68 | 2.38 | 0.7:1 |

Example 4: Summary of Phase III Study: Double-Blind, Placebo-Controlled Crossover Study Inclusive of Two Study Phases A double-blind period (Phase A) and an open label period (Phase B) was performed in patients 6 months through 17 years of age with Pyruvate Dehydrogenase Complex Deficiency (PDCD) (n=34). Patients receiving DCA were dose-stratified according to GSTZ1 genotype. DCA was dosed orally (oral, nasogastric tube, or gastric tube route) at either 12.5 mg/kg (fast metabolizers) or 6.25 mg/kg (slow metabolizers), every 12 hours. Twenty-seven (27) of 34 patients (79%), were fast metabolizers.

The DCA was in the form of an oral solution supplied in 50 mg/mL strength for oral administration and containing the following inactive ingredients: sodium phosphate monobasic, ortho phosphoric acid, thiamine hydrochloride, sodium benzoate, aspartame, glycerin, strawberry flavor, water. The drug product is a clear, colorless solution.

The primary efficacy outcome was assessed using an observer reported outcome that measures motor function, referred to as the $\text{ObsRO}_{motor}$. The $\text{ObsRO}_{motor}$ is a daily observer reported survey that assesses weakness, incoordination, hypotonia (low muscle tone), hypertonia (rigidity, stiff muscle tone), and involuntary movements. Each domain was scored from 0 to 4, where 0 is no presence of the symptom, 1 is mild, 2 is moderate, 3 is severe and 4 extreme, with a total score ranging from 0 to 20.

PDCD is a heterogenous disease with neurologic, metabolic and structural abnormalities. An observer rated Global Health Assessment (GHA) was also used to assess the overall health of the patient in addition to $\text{ObsRO}_{motor}$. GHA was measured each week to assess the prior 7 days using a 5-point scale (much better, better, no change, worse, much worse). GHA scores improved over time and the scores were correlated with $\text{ObsRO}_{motor}$.

Patients with more severe impairment at baseline (N=15) showed greater improvement of motor function in the $\text{ObsRO}_{motor}$ scale vs. placebo (−1.12, p=0.066). Ninety-three percent (93%) of those patients showed improvement in motor function in at least one of the five domains. These improvements extended into the open-label period. The domains with the greatest number of severe patients improving were hypotonia (n=8), involuntary movement (n=6), hypertonia (n=6), weakness (n=6), and incoordination (n=6). Severe patients also improved in several domains measured outside of motor function. Those domains with the greatest number of severe patients improving were sleep (n=8) and fatigue (n=7).

Plasma lactate levels were evaluated as a key biomarker in PDCD. Lactate is a universal marker of disease activity in PDCD, and its elevation is a direct result of the fundamental metabolic deficit. Patients with PDCD have chronically elevated levels of lactate due to decreased PDC activity. Lowering of plasma lactate with use of DCA is considered a biomarker of its activation of PDC.

This clinical trial demonstrated statistically significant and clinically meaningful reductions of 21% in plasma lactate levels in patients treated with DCA vs. placebo (−0.477 mM, p=0.006). Sixty-six percent (66%) of patients on DCA achieved normal levels (≤2 mmol/L) of lactate vs. 42% on placebo (P=0.0114). Patients showed consistent, durable, and statistically significant decreases in lactate while on DCA that continued during the open-label extension phase of the study.

Patients experienced reductions in plasma lactate while on DCA regardless of baseline lactate level, GSTZ1 haplotype status, adherence to a ketogenic diet or $ObsRO_{motor}$ baseline score. Plasma lactate and maintenance of normal levels of plasma lactate were predictive of clinically meaningful improvements in $ObsRO_{motor}$ improved GHA ratings and reduced mortality.

Five of the 34 patients had seizures during the baseline period of the study prior to randomization. One had complete resolution of seizures while on DCA, two had clinically meaningful reductions in the number of seizures, and none worsened while on treatment with DCA.

Benefits of DCA persisted into the open label extension, with 24 of 34 patients maintaining stable disease or achieving clinically meaningful improvement represented by a >20% reduction in $ObsRO_{motor}$. Additionally, >80% of observers rated patients in the trial with a GHA as better or much better during the open-label portion of the study and no observers reported patient worsening.

Observers were asked to fill out a survey during open-label office visits. Twenty-five (25) of the 26 (96.2%) respondents noted improvement in cognition, verbal communication, mobility, and/or endurance Example 5: Survival Study Comparing Outcomes for DCA-Treated Patients in the Phase III Study with External, Untreated Natural History Cohort of Patients with PDCD (n=28)

Efficacy was assessed in a second study by comparing overall survival in pediatric patients with PDCD treated with DCA (n=28) with an untreated natural history cohort of pediatric patients with genetically confirmed PDCD (n=28).

Patients treated with DCA had a statistically significant improvement in overall survival compared to the untreated PDCD patients with a matched historical control group (FIG. 1). The primary endpoint (matched on age and sex) demonstrated a statistically significant multivariate risk reduction of 99% in the relative risk of death for patients with PDCD receiving DCA treatment compared with untreated patients (p=0.0273). Sixty-four percent (64%) of patients in DCA treatment cohort were adherent to a ketogenic diet vs. 71% in the natural history cohort. In this analysis ketogenic diet was not predictive of survival outcomes.

Example 6: Adverse Reaction Data

In the Phase III study, the safety of DCA was assessed in 34 pediatric patients with PDCD aged 6 months to 17 years. Patients receiving DCA were dose-stratified post-randomization according to GSTZ1 genotype to mitigate risk of peripheral neuropathy. DCA was dosed at either 12.5 mg/kg or 6.25 mg/kg divided into two equal doses approximately 12 hours apart. The dose based on GSTZ1 genotyping was done at baseline before patients initiated therapy. As noted above, this Phase III controlled study was followed by an ongoing, open-label extension study, used to assess long term safety and survival outcomes.

Treatment with DCA had an overall incidence of adverse reactions similar to placebo. Generally, adverse reactions were mild. There were no deaths, and no significant adverse effects were determined to be attributed to DCA. The safety profile was similar in both the double-blind and open-label portions of the trial. The most commonly reported adverse reaction occurring in >5% of patients treated with DCA was gastrointestinal disorders (n=2, 5.9%). Table 4 summarizes all adverse reactions that occurred in DCA-treated patients compared to placebo.

TABLE 4

| System Organ Class (SOC)<br>Preferred Term (PT) | DCA<br>(N = 34)<br>n (%) | Placebo<br>(N = 34)<br>n (%) |
|---|---|---|
| Gastrointestinal disorders | 2 (5.9) | 3 (8.8) |
| Constipation | 1 (2.9) | 0 |
| Diarrhea | 1 (2.9) | 0 |
| Flatulence | 0 | 1 (2.9) |
| Salivary hypersecretion | 0 | 1 (2.9) |
| General disorders and administration site conditions | 1 (2.9) | 0 |
| Fatigue | 1 (2.9) | 0 |
| Musculoskeletal and connective tissue disorders | 1 (2.9) | 0 |
| Muscular weakness | 1 (2.9) | 0 |
| Nervous system disorders | 1 (2.9) | 0 |
| Balance disorder | 1 (2.9) | 0 |
| Syncope | 1 (2.9) | 0 |
| Tremor | 1 (2.9) | 0 |
| Psychiatric disorders | 0 | 2 (5.9) |
| Bruxism | 0 | 1 (2.9) |
| Insomnia | 0 | 1 (2.9) |
| Irritability | 0 | 2 (5.9) |
| Skin and subcutaneous tissue disorders | 1 (2.9) | 0 |
| Urticaria | 1 (2.9) | 0 |

N = Number of Patient in Study Cohort,
n = number of patients experiencing adverse reaction,
% = percentage of patient experiencing adverse reaction In the open-label extension study, patients were treated for up to 3 years (median: 1.4 years) with DCA. The adverse events observed during the open-label phase of the study were similar to those observed in the double-blind portion of the study. During the open label portion of the trial there was a report of mild peripheral neuropathy in one patient who later withdrew from the study for a family relocation. This occurred after 18 months and was considered possibly drug related. DCA induced peripheral neuropathy has been identified as reversible upon therapy discontinuation.

Although the present invention has been described in considerable detail with regard to certain versions thereof, other versions are possible, and alterations, permutations and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method for treating pyruvate dehydrogenase complex deficiency (PDCD) with dichloroacetate (DCA) in a PDCD patient on a ketogenic diet having a ratio of calories from fat:(carbohydrates+proteins) that is at least 3:1, the method comprising:

measuring a pre-administration plasma beta-hydroxybutyrate (BHB) level of the patient on the ketogenic diet before initiating DCA treatment, assessing a GSTZ1 haplotype of the patient to determine whether the patient is an EGT carrier or an EGT non-carrier, after measuring the pre-administration plasma BHB level of the patient, orally administering to the patient the DCA in the form of a solution, wherein the DCA is dosed at 25 mg/kg/day when the patient is an EGT carrier, or the DCA is dosed at 12.5 mg/kg/day when the patient is an EGT non-carrier, measuring a post-administration plasma BHB level of the patient after the orally administering the DCA to the patient, after measuring the post-administration plasma BHB level of the patient, administering to the patient a modified diet having a ratio of calories from fat:(carbohydrates+proteins) that ranges from 2.5:1 to 0.7:1, and repeating the orally administering to the patient the DCA, wherein the DCA is dosed at 25 mg/kg/day when the patient is an EGT carrier, or the DCA is dosed at 12.5 mg/kg/day when the patient is an EGT non-carrier, each day the patient is on the modified diet.

* * * * *